United States Patent [19]

Spector

[11] Patent Number: 4,612,223

[45] Date of Patent: Sep. 16, 1986

[54] REVERSIBLE FRAGRANCE EMITTING UNIT

[76] Inventor: Donald Spector, 380 Mountain Rd., Union City, N.J. 07087

[21] Appl. No.: 736,141

[22] Filed: May 20, 1985

[51] Int. Cl.$^4$ .................................................. A61L 9/12
[52] U.S. Cl. .................................... 428/35; D23/150; 215/307; 239/57; 239/60; 428/905
[58] Field of Search ..................... 239/53–59, 239/60; D23/150; 428/35, 905; 215/307

[56] References Cited

U.S. PATENT DOCUMENTS

| D. 162,679 | 3/1951 | Monnecke | D23/150 |
|---|---|---|---|
| 2,414,902 | 1/1947 | Schlumbohm | 215/100 A |
| 2,578,827 | 12/1951 | Munnecke | 239/59 X |
| 2,763,395 | 9/1956 | Meek | 239/58 X |
| 2,766,067 | 10/1956 | Shinberg | 239/58 X |
| 2,982,458 | 5/1961 | Hennion | D7/70 X |
| 4,069,996 | 1/1978 | Koziol | D7/70 X |
| 4,149,675 | 4/1979 | Van Breen et al. | 239/55 X |
| 4,220,281 | 9/1980 | Martens, III et al. | 239/55 X |
| 4,226,829 | 10/1980 | Mike | 239/55 X |
| 4,346,840 | 8/1982 | Gaiser et al. | 239/55 X |
| 4,436,203 | 3/1984 | Reyner | 428/916 X |
| 4,523,870 | 6/1985 | Spector | 239/57 X |
| 4,537,351 | 8/1985 | Wilson | 239/59 X |

Primary Examiner—Henry F. Epstein
Attorney, Agent, or Firm—Michael Ebert

[57] ABSTRACT

A reversible fragrance emitting unit adapted to rest on a table or other flat surface in either an upright position in which the rate of fragrance emission is low, or in an upside down position in which the emission rate is high, the unit having the same attractive outward appearance in either state. The unit consists of a fenestrated open-ended shell having a decorative form whose inlet and outlet ends are attached to inlet and outlet boxes of like dimensions, both having bottom walls. The inlet box has an open top, whereas the outlet box is closed by a top wall to define an internal chamber which extends through the shell between the bottom wall of the inlet box and the top wall of the outlet box. The chamber contains a charge of fragrance-emitting pellets in an amount sufficient to almost fill the inlet box when the unit is placed in its upright position in which the inlet box rests on the table and the pellets are confined within the inlet box and therefore emit relatively little fragrance, the unit being effectively "off". When, however, the unit is reversed to occupy its upside down position in which the outlet box rests on the table, the pellets then occupy the shell and emit fragrance through the openings therein at a much greater rate and the unit is "on".

7 Claims, 5 Drawing Figures

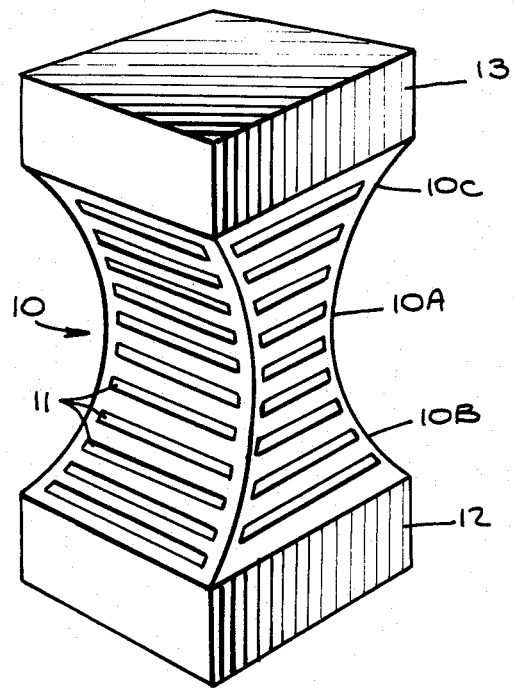
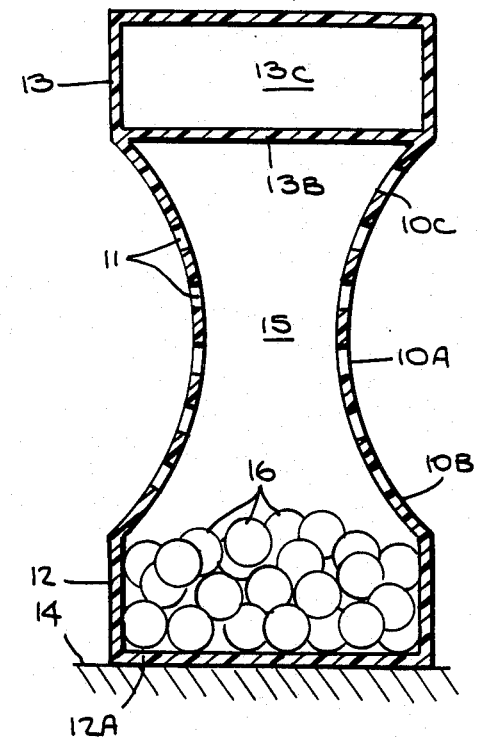
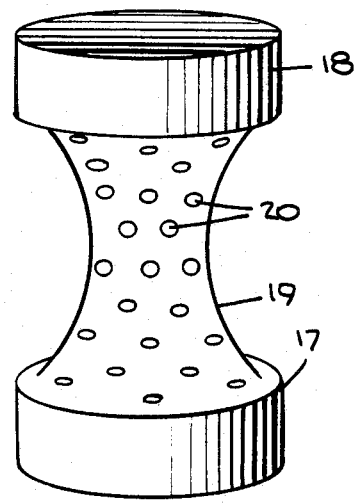
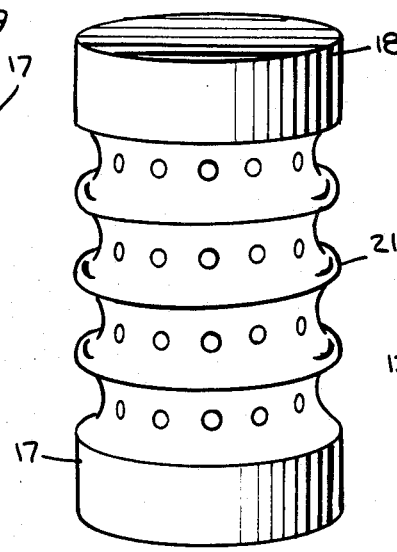
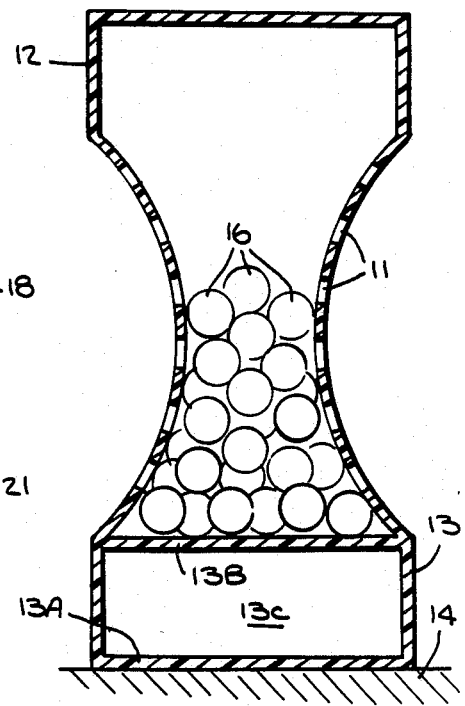

REVERSIBLE FRAGRANCE EMITTING UNIT

BACKGROUND OF INVENTION

1. Field of Invention

This invention relates generally to environmental aroma generators functioning to exude a fragrance into the atmosphere of a room, and more particularly to a reversible fragrance-emitting unit adapted to rest on a table or other flat surface in either an upright position in which the rate of frequency emission is high or in an upside down position in which the emission rate is low.

2. Status of Prior Art

As used herein, the term "aroma" or "fragrance" is not limited to pleasant or savory smells but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and other yielding altogether new scents. Perfumes today are largely blends of natural and synthetic scents and of fixatives which equalize vaporization and enhance pungency. In most liquid scents, the ingredients are combined with a highly volatile alcohol carrier.

There are many situations in which the environment of a living room, a kitchen, an office or other enclosure occupied by people is rendered unpleasant by tobacco smoke, food smells or other pungent odors. It is often not practical, as in the winter months, to open a window or operate an air conditioner to clear the air. The common practice, therefore, is to mask or modify the prevailing atmosphere by some sort of air freshener device or aroma generator.

In some situations, the atmosphere of a room may be clear and free of odors, yet it may be desirable to introduce a fragrance in order to create a more romantic ambience or to induce other effects, for personal moods are highly influenced by odors. Thus the effect of a musk-like odor is very different from that of sea air and such differences can be exploited when manipulating the environment.

It is known to provide an air freshener or fragrance generator in the form of a bottle containing a volatile liquid in which a wick is immersed, the upper end of the wick extending above the bottle and being exposed to the air. Such devices not only are subject to spillage or leakage, but, in order to adjust the rate of volatilization, means must be provided to vary the extent of wick exposure.

The U.S. Pat. No. to Meek, 2,763,395, discloses an air freshener in which a vented cylindrical container is filled with particles of absorbent material impregnated with a volatile air-freshener liquid. The vented container is telescoped within a cylindrical housing and is provided with detents making it possible to more or less raise the vented container relative to its housing and thereby more or less expose the impregnated particles to the atmosphere. In this way, one can adjust the rate of odor or air freshener dissemination. A vapor dispenser having telescoping elements to adjust the rate of dissemination is also shown in the Martens et al. U.S. Pat. No. 4,220,281.

In the Munnecke Pat. No. 2,578,827, a deodorized unit is disclosed in which an absorbent filler held in a container is impregnated with a volatile liquid. In this unit the rate of emission is controlled by an adjustable shutter in which two sets of holes are more or less brought into registration with each other.

Apart from the mechanical complexity of the units disclosed in the above-identified patents, is the fact that they have an appearance that is strictly utilitarian and devoid of aesthetic appeal. The functional character of these units is not objectionable when they are installed in a workplace or kitchen. But in a living room or in other well-appointed enclosures, odor emitting units of the prior art type strike a discordant note, and they are usually not acceptable. Where one wishes to conceal the source of scent emission and give the impression that the atmosphere is naturally agreeable, this purpose is not served by prior art forms of aroma generators whose true function is undisguised.

SUMMARY OF INVENTION

In view of the foregoing, the main object of this invention is to provide a fragrance emitting unit having a pleasing decorative appearance which renders it acceptable in a well-appointed room or other enclosure, the rate of fragrance emission being adjustable from an almost "off" to a full "on" rate without the need for mechanical expedients.

More particularly, an object of this invention is to provide a reversible unit of the above type which is adapted to rest on a table or other flat surface in either an upright position in which the unit effectively is "off", or in an upside down position in which the unit is "on", the appearance of the unit being the same in either position.

Also an object of the invention is to provide an attractive, low-cost unit which may be mass produced.

Briefly stated, these objects are attained in a reversible fragrance emitting unit adapted to rest on a table or other flat surface in either an upright position in which the rate of fragrance emission is low, or in an upside down position in which the emission rate is high, the unit having the same attractive outward appearance in either state. The unit consists of a fenestrated open-ended shell having a decorative form whose inlet and outlet ends are attached to inlet and outlet boxes of like dimensions, both having bottom walls. The inlet box has an open top, whereas the outlet box is closed by a top wall to define an internal chamber which extends through the shell between the bottom wall of the inlet box and the top wall of the outlet box. The chamber contains a charge of fragrance-emitting pellets in an amount sufficient to almost fill the inlet box when the unit is placed in its upright position in which the inlet box rests on the table and the pellets are confined within the inlet box and therefore emit relatively little fragrance, the unit being effectively "off". When, however, the unit is reversed to occupy its upside down position in which the outlet box rests on the table, the pellets then occupy the shell and emit fragrance through the openings therein at a much greater rate and the unit is "on".

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of one preferred embodiment of a fragrance emitting unit in accordance with the invention showing it in its upright position in which the unit is "off";

FIG. 2 is a longitudinal section taken through the FIG. 1 unit;

FIG. 3 shows, in section, the unit in its upside down "on" position;

FIG. 4 illustrates, in perspective, a second embodiment of the unit; and

FIG. 5 illustrates, in perspective, a third embodiment of the unit.

DESCRIPTION OF INVENTION

First Embodiment

Referring now to FIGS. 1, 2 and 3, a fragrance emitting unit in accordance with the invention includes an open-ended fenestrated shell 10 which may be formed of synthetic plastic or other material which is provided on all sides with an array of slots 11 forming air vents.

In the shell shown in FIG. 1, the shell has a Venturi-like or hourglass configuration forming a constricted throat 10A which on one side joins a converging inlet section 10B and on the other side joins a diverging outlet section 10C. The mouth of the inlet section 10B is attached to a rectangular inlet box 12, and the mouth of the outlet section 10C is attached to a rectangular outlet box 13 whose dimensions are the same as that of the inlet box 12.

In FIGS. 1 and 2, the unit is shown in its upright or "off" position, in which the inlet box 12 rests on a table 14 or some other flat surface 14, in which case outlet box 13 is perched on top of shell 10. Inlet box 12 has a bottom wall 12A, but its top is open, whereas outlet box 13 has a bottom wall 13A and a top wall 13B so that the interior 13C thereof is sealed, thereby defining an internal chamber 15 which extends from the bottom wall 12A of the inlet box 12 to the top wall 13B of outlet box 13.

Contained in chamber 15 is a charge of pellets 16 in an amount sufficient to almost fill open-top inlet box 12 when this box rests on surface 14, this being the upright position of the unit, in which state the outlet box 13 is perched on shell 10. Pellets 16 may be formed by small porous balls of open-cell foam plastic material, a porous ceramic or any other absorbent material. These pellets are impregnated with a volatile liquid fragrance so that the pellets, when exposed to the atmosphere, emit a fragrance. Or the pellets may be formed of a plastic material in which a volatile liquid fragrance is dispersed therein to render the plastic emissive. The choice of aroma or fragrance depends on the intended use of the unit, and it may be constituted by an air freshener, an insecticide or a deodorant.

In the upright position shown in FIGS. 1 and 2, the charge of pellets 16 then lie within inlet box 12; hence only the upper surface of the charge is exposed, all other sides of the charge being shielded from the atmosphere by the sides and bottom of the inlet box. As a consequence, very little fragrance is emitted from the unit and the unit is effectively "off".

In order to turn on the unit, one has merely to turn it upside down so that outlet box 13 in this position then rests on a surface 14, as shown in FIG. 3. In this state, the charge of pellets 16 lies on the top wall 13B of the outlet box 13 and the charge then almost fills the shell 10. As a consequence, the charge is much more exposed to the atmosphere, and the rate of fragrance emission is high. This is the "on" condition of the unit.

Thus, no mechanical expedients are required to switch the unit "on" and "off", for one has merely to reverse its position on the table in the manner of an hourglass. The symmetry of the unit is such that in either state, its outward appearance is the same. The hourglass configuration of the unit imparts an attractive appearance thereto, so that it does not have the utilitarian look of a typical air freshener, and it may be placed on a table in a well-appointed living room without disturbing the decor.

In practice, the outer surfaces of the bottom walls of the unit may be coated or otherwise treated to render them reflective so that they function as mirrors to heighten the aesthetic appeal of the unit. Or the entire unit may be made of white or black plastic to render it relatively inconspicuous and starkly simple in keeping with modern minimalist decor trends.

Other Embodiments

Instead of a unit provided with rectangular inlet and outlet boxes joined to a Venturi-like shell as in FIG. 1, the unit, as shown in FIG. 4, may be formed with inlet and outlet boxes 17 and 18 in a circular configuration joined to a shell 19 having a round form more closely approaching that of an hourglass.

The advantage of an hourglass-shaped shell 19 is that it is of progressively reduced cross-sectional diameter as one goes from one end thereof to its constricted throat. As a result, its interior volume is smaller than that of a cylindrical shell; hence the pellets 16 in the upright position which are in an amount sufficient to just about fill the inlet box, will then almost fill the shell to provide greater exposure of the pellets and a higher rate of emission.

In the form shown in FIG. 1, the shell is vented by horizontal slots 11; but in practice, as shown in FIG. 4, the shell openings 20 may be small circular bores to impart a different appearance to the unit without altering its function.

Or, as shown in FIG. 5, shell 21, instead of being in hourglass form, may be in the shape of a corrugated cylinder having small bores therein to provide vents. It will be appreciated that the operation of the units in FIGS. 4 and 5 is essentially the same as that in FIG. 1.

While there have been shown and described preferred embodiments of REVERSIBLE FRAGRANCE EMITTING UNIT in accordance with the invention, it will be appreciated that many changes and modifications may be made therein without, however, departing from the essential spirit thereof.

Thus, instead of using fragrance pellets, one may use a liquid fragrance in an amount sufficient to fill the inlet box. In this case, instead of a shell having holes therein, the shell will be made of a plastic which is vapor permeable. Thus, when the unit is upside down and the liquid is then within the shell, it will exude an aromatic vapor at a high rate through the vapor-permeable shell.

I claim:

1. A reversible fragrance emitting unit adapted to rest on a flat surface in either an upright position in which the rate of fragrance emission is low and the unit is effectively "off", or in an upside down position in which the emission rate is high and the unit is "on", the unit comprising:

A a fenestrated open-ended shell;

B an inlet box attached to one end of the shell and having a bottom wall and an open top whereby this box communicates with the shell;
C an outlet box attached to the other end of the shell and having a bottom wall and a top wall whereby the interior of this box is sealed from the shell, said boxes in combination with said shell defining an interior chamber extending from the bottom wall of the inlet box to the top wall of the outlet box; and
D a charge of fragrance-emitting pellets entrapped in said chamber in an amount sufficient to substantially fill the inlet box when the unit is placed on the flat surface in its upright position, in which state there is relatively little emission from the charge into the atmosphere, the pellets occupying the fenestrated shell in the upside down position of the unit, in which state the emission rate is high.

2. A unit as set forth in claim 1, wherein said boxes have identical dimensions to form a symmetrical structure.

3. A unit as set forth in claim 2, wherein said boxes have a rectangular form and said shell has a Venturi-like form.

4. A unit as set forth in claim 1, wherein said pellets are formed of porous plastic material impregnated with a volatile liquid.

5. A unit as set forth in claim 1, wherein said pellets are formed of a porous ceramic material impregnated with a liquid fragrance.

6. A unit as set forth in claim 1, wherein said boxes have a cylindrical form and said shell has an hourglass configuration.

7. A unit as set forth in claim 1, wherein said boxes have a cylindrical form and said shell has a corrugated cylindrical form.

* * * * *